(12) United States Patent
Flanders et al.

(10) Patent No.: US 8,670,129 B2
(45) Date of Patent: Mar. 11, 2014

(54) FILTERED ASE SWEPT SOURCE FOR OCT MEDICAL IMAGING

(75) Inventors: Dale C. Flanders, Lexington, MA (US); Walid A. Atia, Lexington, MA (US); Mark E. Kuznetsov, Lexington, MA (US)

(73) Assignee: Axsun Technologies, Inc., Billerica, MA (US)

( * ) Notice: Subject to any disclaimer, the term of this patent is extended or adjusted under 35 U.S.C. 154(b) by 729 days.

(21) Appl. No.: 12/553,295

(22) Filed: Sep. 3, 2009

(65) Prior Publication Data

US 2011/0051148 A1    Mar. 3, 2011

(51) Int. Cl.
*G01B 9/02*    (2006.01)

(52) U.S. Cl.
USPC .......................................... 356/519; 356/491

(58) Field of Classification Search
USPC .................................. 356/519, 491
See application file for complete search history.

(56) References Cited

U.S. PATENT DOCUMENTS

| | | | |
|---|---|---|---|
| 3,914,055 A | 10/1975 | Wolga et al. |
| 4,466,699 A | 8/1984 | Droessler et al. |
| 4,929,063 A | 5/1990 | Durand et al. |
| 4,989,216 A | 1/1991 | Chandra et al. |
| 5,263,037 A | 11/1993 | Trutna, Jr. et al. |
| 5,321,501 A | 6/1994 | Swanson et al. |
| 5,430,574 A | 7/1995 | Tehrani |
| 5,434,943 A | 7/1995 | Dentai et al. |
| 5,459,570 A | 10/1995 | Swanson et al. |
| 5,465,147 A | 11/1995 | Swanson |
| 5,475,221 A | 12/1995 | Wang |
| 5,500,762 A | 3/1996 | Uchiyama et al. |
| 5,509,093 A | 4/1996 | Miller et al. |
| 5,537,634 A | 7/1996 | Fye |
| 5,574,739 A | 11/1996 | Carruthers et al. |
| 5,600,466 A | 2/1997 | Tsushima et al. |
| 5,619,368 A | 4/1997 | Swanson |

(Continued)

FOREIGN PATENT DOCUMENTS

DE    4122925 A1    1/1993
DE    10 2008 045 634 A1    3/2010

(Continued)

OTHER PUBLICATIONS

Grant Fowles, Introduction to Modern Optics, 1975, Dover, Second edition, p. 85-91.*

(Continued)

*Primary Examiner* — Jonathan Hansen
(74) *Attorney, Agent, or Firm* — Houston & Associates, LLP

(57) ABSTRACT

An integrated swept wavelength optical source uses a filtered ASE signal with an optical amplifier and tracking filter. This source comprises a micro optical bench, a source for generating broadband light, a first tunable Fabry Perot filter, installed on the bench, for spectrally filtering the broadband light from the broadband source to generate a narrowband tunable signal, an amplifier, installed on the bench, for amplifying the tunable signal, and a second tunable Fabry Perot filter, installed on the bench, for spectrally filtering the amplified tunable signal from the amplifier. A self-tracking arrangement is also possible where a single tunable filter both generates the narrowband signal and spectrally filters the amplified signal. In some examples, two-stage amplification is provided. The use of a single bench implementation yields a low cost high performance system. For example, polarization control between components is no longer necessary.

3 Claims, 10 Drawing Sheets

(56) References Cited

U.S. PATENT DOCUMENTS

| | | |
|---|---|---|
| 5,627,668 A | 5/1997 | Fye |
| 5,646,729 A | 7/1997 | Koskinen et al. |
| 5,724,373 A | 3/1998 | Chang |
| 5,742,418 A | 4/1998 | Mizutani et al. |
| 5,748,598 A | 5/1998 | Swanson et al. |
| 5,784,352 A | 7/1998 | Swanson et al. |
| 5,808,788 A | 9/1998 | Park et al. |
| 5,818,586 A | 10/1998 | Lehto et al. |
| 5,956,355 A | 9/1999 | Swanson et al. |
| 5,991,477 A | 11/1999 | Ishikawa et al. |
| 6,111,645 A | 8/2000 | Tearney et al. |
| 6,134,003 A | 10/2000 | Tearney et al. |
| 6,160,826 A | 12/2000 | Swanson et al. |
| 6,191,862 B1 | 2/2001 | Swanson et al. |
| 6,204,920 B1 | 3/2001 | Ellerbrock et al. |
| 6,282,011 B1 | 8/2001 | Tearney et al. |
| 6,282,215 B1 | 8/2001 | Zorabedian et al. |
| 6,339,603 B1 | 1/2002 | Flanders et al. |
| 6,345,059 B1 | 2/2002 | Flanders |
| 6,357,913 B1 | 3/2002 | Kim et al. |
| 6,359,724 B1 | 3/2002 | Katagiri et al. |
| 6,373,632 B1 | 4/2002 | Flanders |
| 6,377,386 B1 | 4/2002 | Korn |
| 6,381,022 B1 | 4/2002 | Zavracky |
| 6,407,376 B1 | 6/2002 | Korn et al. |
| 6,421,164 B2 | 7/2002 | Tearney et al. |
| 6,445,939 B1 | 9/2002 | Swanson et al. |
| 6,473,234 B2 | 10/2002 | Kuznetsov |
| 6,485,413 B1 | 11/2002 | Boppart et al. |
| 6,490,074 B1 | 12/2002 | Korn |
| 6,501,551 B1 | 12/2002 | Tearney et al. |
| 6,510,261 B2 | 1/2003 | Sorin et al. |
| 6,552,796 B2 | 4/2003 | Magnin et al. |
| 6,564,087 B1 | 5/2003 | Pitris et al. |
| 6,570,659 B2 | 5/2003 | Schmitt |
| 6,608,711 B2 | 8/2003 | Flanders et al. |
| 6,619,864 B2 | 9/2003 | Johnson et al. |
| 6,639,666 B2 | 10/2003 | Li |
| 6,706,004 B2 | 3/2004 | Tearney et al. |
| 6,816,515 B1 | 11/2004 | Yun et al. |
| 6,845,121 B2 | 1/2005 | McDonald |
| 6,853,654 B2 | 2/2005 | McDonald et al. |
| 6,862,136 B2 | 3/2005 | Koren et al. |
| 6,879,619 B1 | 4/2005 | Green et al. |
| 6,879,851 B2 | 4/2005 | McNamara et al. |
| 6,888,856 B2 | 5/2005 | Green et al. |
| 6,891,984 B2 | 5/2005 | Petersen et al. |
| 6,901,087 B1 * | 5/2005 | Richardson et al. ............ 372/20 |
| 6,905,255 B2 | 6/2005 | Flanders et al. |
| 6,999,491 B2 | 2/2006 | Rieger et al. |
| 7,027,198 B2 | 4/2006 | Yao |
| 7,061,618 B2 | 6/2006 | Atia et al. |
| 7,075,058 B2 | 7/2006 | Chinn et al. |
| 7,110,169 B1 | 9/2006 | Walker et al. |
| 7,120,176 B2 | 10/2006 | McDonald et al. |
| 7,157,712 B2 | 1/2007 | Flanders et al. |
| 7,208,333 B2 | 4/2007 | Flanders et al. |
| 7,218,436 B2 | 5/2007 | Yao |
| 7,231,243 B2 | 6/2007 | Tearney et al. |
| 7,241,286 B2 | 7/2007 | Atlas |
| 7,242,509 B2 | 7/2007 | Atia et al. |
| 7,292,344 B2 | 11/2007 | Atia et al. |
| 7,349,631 B2 | 3/2008 | Lee et al. |
| 7,391,520 B2 | 6/2008 | Zhou et al. |
| 7,406,107 B2 | 7/2008 | Flanders et al. |
| 7,414,779 B2 | 8/2008 | Huber et al. |
| 7,415,049 B2 | 8/2008 | Flanders et al. |
| 7,613,398 B2 | 11/2009 | Lee et al. |
| 7,625,366 B2 | 12/2009 | Atlas |
| 7,813,609 B2 | 10/2010 | Petersen et al. |
| 7,848,791 B2 | 12/2010 | Schmitt et al. |
| 7,884,945 B2 | 2/2011 | Srinivasan et al. |
| 7,903,979 B2 | 3/2011 | Lee et al. |
| 7,916,387 B2 | 3/2011 | Schmitt |
| 7,935,060 B2 | 5/2011 | Schmitt et al. |
| 2001/0013934 A1 | 8/2001 | Varnham et al. |
| 2002/0054614 A1 | 5/2002 | Jin |
| 2002/0161351 A1 | 10/2002 | Samson et al. |
| 2003/0107745 A1 | 6/2003 | Atia et al. |
| 2003/0179790 A1 | 9/2003 | Bouda et al. |
| 2005/0078716 A1 | 4/2005 | Liu |
| 2005/0083533 A1 * | 4/2005 | Atia et al. ..................... 356/454 |
| 2005/0201662 A1 | 9/2005 | Petersen et al. |
| 2005/0265402 A1 | 12/2005 | Tanaka et al. |
| 2006/0072112 A1 * | 4/2006 | Flanders et al. ............. 356/432 |
| 2006/0072632 A1 | 4/2006 | Flanders et al. |
| 2006/0095065 A1 | 5/2006 | Tanimura et al. |
| 2006/0109872 A1 | 5/2006 | Sanders |
| 2006/0187537 A1 | 8/2006 | Huber et al. |
| 2007/0013917 A1 | 1/2007 | Stubbe et al. |
| 2008/0165366 A1 * | 7/2008 | Schmitt ........................ 356/519 |
| 2009/0174931 A1 | 7/2009 | Huber et al. |
| 2009/0245304 A1 * | 10/2009 | Peng et al. ................. 372/29.02 |
| 2009/0306520 A1 | 12/2009 | Schmitt et al. |
| 2009/0323080 A1 * | 12/2009 | Toida ........................... 356/511 |
| 2010/0076320 A1 | 3/2010 | Petersen et al. |
| 2010/0094127 A1 | 4/2010 | Xu |
| 2010/0103964 A1 | 4/2010 | Huber |
| 2010/0128348 A1 | 5/2010 | Taverner |
| 2010/0253949 A1 | 10/2010 | Adler et al. |
| 2011/0007315 A1 | 1/2011 | Petersen et al. |
| 2011/0051143 A1 | 3/2011 | Flanders et al. |
| 2011/0071404 A1 | 3/2011 | Schmitt et al. |
| 2011/0101207 A1 | 5/2011 | Schmitt |
| 2011/0157686 A1 | 6/2011 | Huber et al. |

FOREIGN PATENT DOCUMENTS

| | | |
|---|---|---|
| EP | 0 501 559 A1 | 9/1992 |
| EP | 0524382 B1 | 1/1993 |
| EP | 0709659 A2 | 5/1996 |
| EP | 0469259 B1 | 8/1996 |
| EP | 0911655 A2 | 4/1999 |
| EP | 1 744 119 A1 | 1/2007 |
| EP | 1020969 B1 | 3/2007 |
| FR | 2704651 A1 | 11/1994 |
| GB | 2118768 A | 11/1983 |
| GB | 2317045 A | 3/1998 |
| JP | 63092917 A | 4/1988 |
| JP | 8148744 A | 6/1996 |
| WO | 0165734 A2 | 9/2001 |
| WO | 03/046630 A1 | 6/2003 |
| WO | 03096106 A1 | 11/2003 |
| WO | 2006/039091 A2 | 4/2006 |
| WO | 2006/039154 A1 | 4/2006 |
| WO | 2008/135034 A1 | 11/2008 |
| WO | 2010/026197 A2 | 3/2010 |

OTHER PUBLICATIONS

Chen, D. et al., "Fiber Bragg Grating Interrogation for a Sensing System Based on a Continuous-Wave Fourier Domain Mode Locking Fiber Laser," Optical Society of America, Conference on Lasers and Electro-Optics (CLEO)/Quantum Electronics and Laser Science (QELS), Piscataway, NJ, May 4, 2008, pp. 1-2.

Eom, T. J. et al., "Narrowband wavelength selective detector applicable SD-OCT based on Fabry-Perot tunable filter and balanced photoreceiver," Coherence Domain Optical Methods and Optical Coherence Tomography in Biomedicine XII, SPIE vol. 6847, Jan. 21, 2008, pp. 1-7.

Huber, R. et al., "Fourier Domain Mode Locking (FDML): A new laser operating regime and applications for optical coherence tomography," Optical Society of America, Optics Express, vol. 14, No. 8, Apr. 17, 2006, pp. 3325-3237.

Nielsen, F. D. et al., "Semiconductor optical amplifier based swept wavelength source at 1060nm using a scanning Fabry-Perot filter and an YDFA-based booster amplifier," Coherence Domain Optical Methods and Optical Coherence Tomography in Biomedicine XI, SPIE vol. 6429, Jan. 2007, pp. 1-8.

International Search Report, completed on May 31, 2011, from counterpart International Application No. PCT/US2010/047813, filed on Sep. 3, 2010.

(56) References Cited

OTHER PUBLICATIONS

Bogatov, A. P., "Anomalous Interaction of spectral Modes in a Semiconductor Laser," IEEE Journal of Quantum Electronics, vol. QE-11, No. 7, Jul. 1975, pp. 510-515.

Eigenwillig, C., "Wavelength swept amplified spontaneous emission source," Optics Express, vol. 17, No. 21, Oct. 12, 2009, pp. 18794-18807.

Eigenwillig, C., "Wavelength swept ASE source," Optical Coherence Tomography and Coherence Techniques IV, edited by Peter E. Anderson, Proc. of SPIE-OSA Biomedical Optics, SPIE vol. 7372, 2009, pp. 737200-1 to 737200-6.

Huber, R., et al, "Amplified, frequency swept lasers for frequency domain reflectometry and OCT imaging: design and scaling principles," Optics Express, vol. 13, No. 9, May 2, 2005, pp. 3513-3528.

Kang, J., "Simple fiber-optic source for optical coherence tomography," SPIE Newsroom, 2008, 2 pages.

Nielson, F. D., et al, "Swept-wavelength source for optic coherence tomography in the 1 µm range," Optics Express, vol. 13, Issue 11, May 2005, pp. 4096-4106.

Pan, J.J., et al, "Fiber Sources: High-power ASE tunable lasers show their colors," Laser Focus World, 2007, available at www.laserfocusworld.com/ARTICLES/308971, 4 pages.

Sheoran, G., et al., "Swept-source digital holography to reconstruct tomographic images," Optics Letters, vol. 34, No. 12, Jun. 15, 2009, pp. 1879-1881.

Tang, Yibing, et al., "A powerful new tool for medical imaging and industrial measurement," SPIE Newsroom, 2008, 2 pages.

International Preliminary Report on Patentability dated Mar. 15, 2012 from counterpart International Application No. PCT/US2010/047813, filed Sep. 3, 2010.

Aljada, M. et al., "Experimental demonstration of a tunable laser using an SOA and an Opto-VLSI Processor," Optics Express, vol. 15, No. 15, Jul. 23, 2007, pp. 9666-9671.

Chang, T. et al., "Pulsed Dye-Laser with Grating and Etalon in a Symmetric Arrangement," Appl. Opt., vol. 19, No. 21, 1980, pp. 3651-3654.

Coquin, G. et al., "Single- and multiple-wavelength operation of acoustooptically tuned semiconductor lasers at 1.3 µm," IEEE Journal of Quantum Electronics, vol. 25, No. 6, Jun. 1989, pp. 1575-1579.

Huber, R. et al., "Fourier Domain Mode Locked Lasers for OCT imaging at up to 290 kHz sweep rates," Proceedings of the SPIE, OSA Biomedical Optics, vol. 5861, 2005, pp. 58611B-1 to 58611B-6.

Klauminzer, GK, "Etalon-Grating Synchronized Scanning of a Narrowband Pulsed Dye Laser," Optical Engineering, vol. 13, No. 6, 1974; pp. 528-530.

Kowalski, F.V. et al., "Optical pulse generation with a frequency shifted feedback laser," Applied Physics Letters, vol. 53, No. 9, Aug. 1988, pp. 734-736.

Oshiba, S. et al., "Tunable fiber ring lasers with an electronically accessible acousto-optic filer," Photonic Switching II, Proceedings of the International Topical Meeting, Kobe, Japan, Apr. 1990, pp. 241-244.

Shimizu, K. et al., "Measurement of Rayleigh Backscattering in Single-Mode Fibers Based on Coherent OFDR Employing a DFB Laser Diode," IEEE Photonics Technology Letters, vol. 3, No. 11, 1991, pp. 1039-1041.

Takada, K. et al., "Loss distribution measurement of silica-based waveguides by using a jaggedness-free optical low coherence reflectometer," Electronics Letters, vol. 30, No. 17, Aug. 18, 1994, pp. 1441-1443.

Takada, K. et al., "Rapidly-tunable narrowband light source with symmetrical crossing configuration for low coherence reflectometry," Electronics Letter, Jan. 5, 1995, vol. 31, No. 1, pp. 63-65.

Takada, K. et al., "Tunable Narrow-Band Light Source Using Two Optical Circulators," IEEE Photonics Technology Letters, vol. 9, No. 1, 1997, pp. 91-93.

Takesue, H. et al., "Broad-Band Lightwave Synthesized Frequency Sweeper Using Synchronous Filtering," Journal of Lightwave Technology, vol. 22, No. 3, Mar. 2004, pp. 755-762.

Telle, J.M. et al., "Very rapid tuning of cw dye laser," Applied Physics Letters, vol. 26, No. 10, 1975, pp. 572-574.

Yun, S.H. et al., "High-speed wavelength-swept semiconductor laser with a polygon-scanner-based wavelength filter," Optics Letters, vol. 28, No. 20, 2003, pp. 1981-1983.

Yun, S.H. et al., "Interrogation of fiber grating sensor arrays with a wavelength-swept fiber laser," Optics Letters, vol. 23, No. 11, 1998, pp. 843-845.

Yun, S.H. et al., "Wavelength-Swept Fiber Laser with Frequency Shifted Feedback and Resonantly Swept Intra-Cavity Acousto-Optic Tunable Filter," IEEE Journal of Selected Topics in Quantum Electronics, vol. 3, No. 4, 1997, pp. 1087-1096.

Eigenwillig, C.M. et al., "Wavelength swept amplified spontaneous emission source for high speed retinal optical coherence tomography at 1060 nm," Journal of Biophotonics, 2010, pp. 1-7.

Brochure, "Agilent 83437A Broadband Light Source and Agilent 83438A Erbium ASE Source, Product Overview," Agilent Technologies, 1996, 2002.

Gmachl, C. et al., "Ultra-broadband semiconductor laser," Nature, vol. 415, Feb. 21, 2002, pp. 883-887.

Krawczyk, S. K. et al., "GaN and Related Compunds for MEMS and MOEMS," Aromagraph DC 2000 System, vol. 51, No. 8, 1999, pp. 623-625.

Vakhshoori, D. et al., "Raman Amplification Using High-Power Incoherent Semiconductor Pump Sources," Ahara Corporation, MA, 2003.

Zhao, M., et al. "Analysis and Optimization of Intensity Noise Reduction in Spectrum-Sliced WDM Systems Using a Saturated Semiconductor Optical Amplifier," IEEE Photonics Technology Letters, vol. 14, No. 3, pp. 390-392, Mar. 2002.

\* cited by examiner

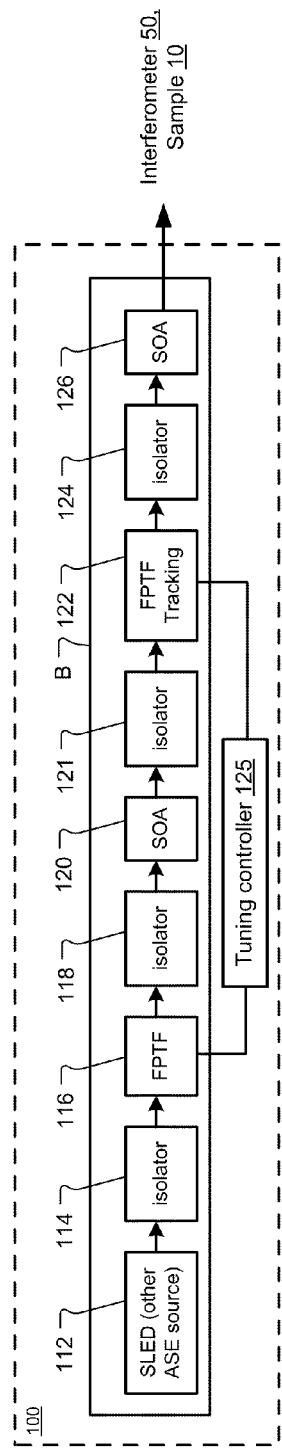
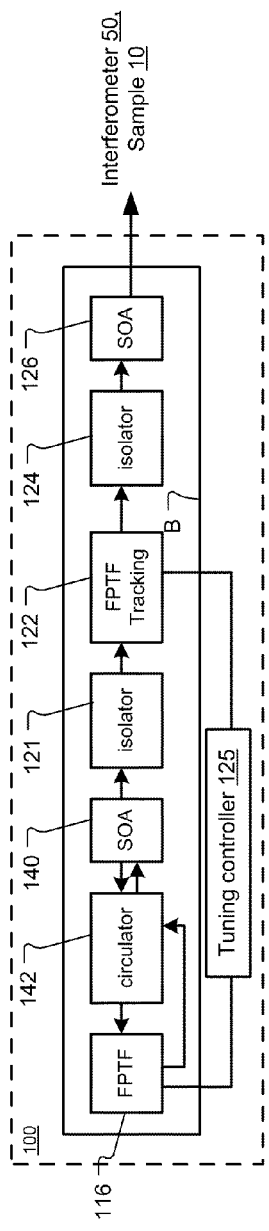
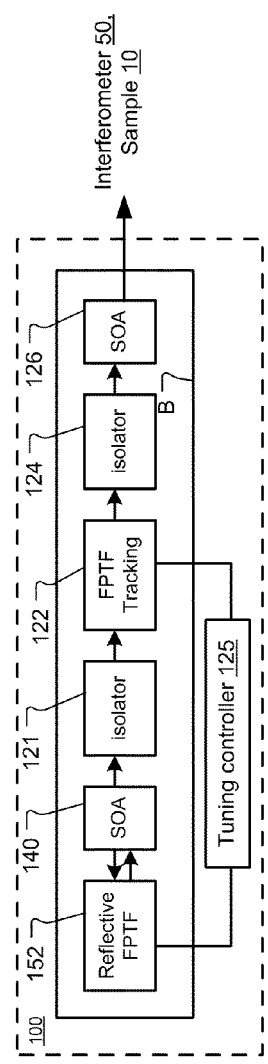
Fig. 1
Fig. 2
Fig. 3A

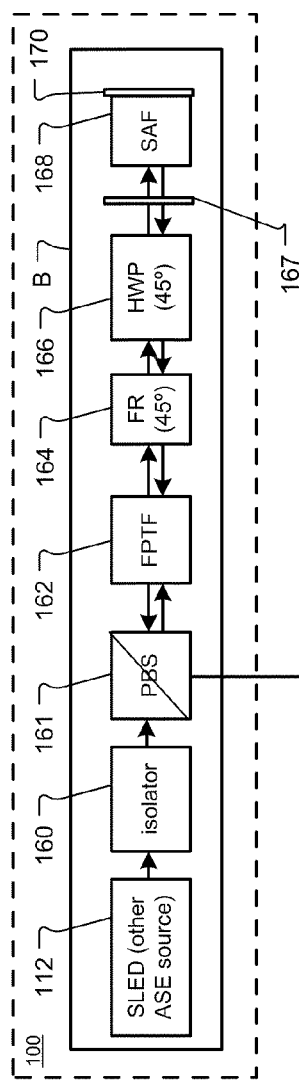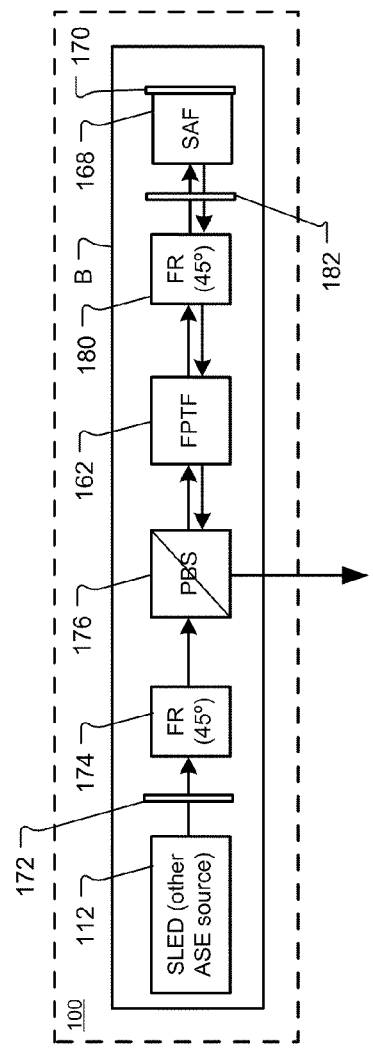

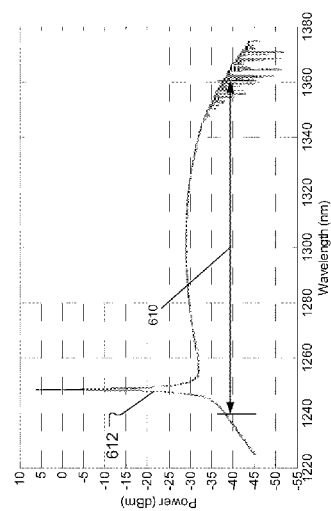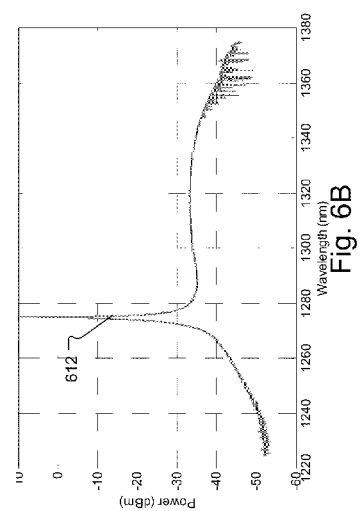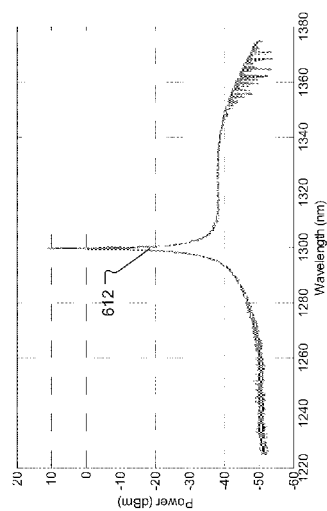

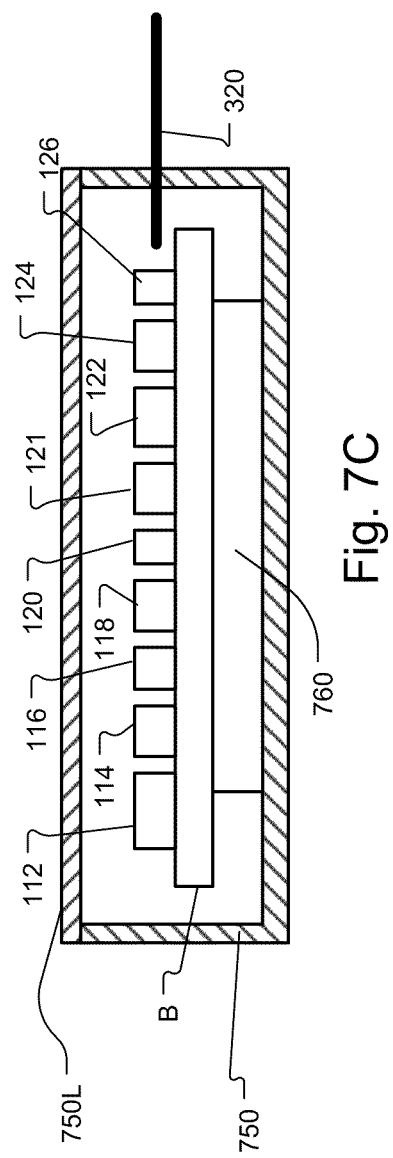

FILTERED ASE SWEPT SOURCE FOR OCT MEDICAL IMAGING

BACKGROUND OF THE INVENTION

Optical coherence analysis relies on the use of the interference phenomena between a reference wave and an experimental wave or between two parts of an experimental wave to measure distances and thicknesses, and calculate indices of refraction of a sample. Optical Coherence Tomography (OCT) is one example technology that is used to perform usually high-resolution cross sectional imaging. It is often applied to imaging biological tissue structures, for example, on microscopic scales in real time. Optical waves are reflected from an object or sample and a computer produces images of cross sections of the object by using information on how the waves are changed upon reflection.

The original OCT imaging technique was time-domain OCT (TD-OCT), which used a movable reference mirror in a Michelson interferometer arrangement. More recently Fourier domain OCT (FD-OCT) has been developed. Two related FD-OCT techniques are time encoded and spectrum encoded OCT. These Fourier domain techniques use either a wavelength swept source and a single detector, sometimes referred to as time-encoded FD-OCT (TEFD-OCT) or swept source OCT, or, alternatively, a broadband source and spectrally resolving detector system, sometimes referred to as spectrum-encoded FD-OCT or SEFD-OCT. These three OCT techniques parallel the three spectroscopy approaches of Fourier Transform spectrometer, a tunable laser spectrometer, and dispersive grating with detector array spectrometer.

These various OCT techniques offer different performance characteristics. FD-OCT has advantages over time domain OCT (TD-OCT) in speed and signal-to-noise ratio (SNR). Of the two Fourier Domain OCT techniques, swept-source OCT or TEFD-OCT has distinct advantages over SEFD-OCT because of its capability of balanced and polarization diversity detection; it has advantages as well for imaging in wavelength regions where inexpensive and fast detector arrays are not available.

TEFD-OCT or swept source OCT has advantages over SEFD-OCT in some additional respects. The spectral components are not encoded by spatial separation, but they are encoded in time. The spectrum is either filtered or generated in successive frequency steps and reconstructed before Fourier-transformation. Using the frequency scanning swept source the optical configuration becomes less complex but the critical performance characteristics now reside in the source and especially its tuning speed and accuracy.

The swept sources for TEFD-OCT systems have been typically tunable lasers. The advantages of tunable lasers include high spectral brightness and relatively simple optical designs. The typical tunable laser is constructed from a gain medium, such as a semiconductor optical amplifier (SOA), and a tunable filter such as a rotating grating, grating with a rotating mirror, or a Fabry-Perot tunable filter. Currently, some of the highest speed TEFD-OCT lasers are based on the laser designs described in U.S. Pat. No. 7,415,049 B1, entitled Laser with Tilted Multi Spatial Mode Resonator Tuning Element, by D. Flanders, M. Kuznetsov and W. Atia. This highly integrated design allows for a short laser cavity that keeps the round-trip optical travel times within the laser short so that the laser is fundamentally capable of high speed tuning Secondly, the use of micro-electro-mechanical system (MEMS) Fabry-Perot tunable filters combines the capability for wide spectral scan bands with the low mass high mechanical resonant frequency deflectable MEMS membranes that can be tuned quickly.

Another swept laser source for OCT is the Frequency Domain Modelocked Laser (FDML) as described in U.S. Pat. No. 7,414,779 B2. FDML lasers use semiconductor optical amplifiers in a very long, kilometer or more, fiber ring cavity that requires polarization control and active length stabilization.

The use of laser-based swept sources, however, does create problems. The instantaneous laser emission is characterized by one or more longitudinal laser cavity modes that simultaneously lase within the passband of the laser's tunable filter. Then as the laser tunes, the power within these modes shifts between the modes and to new cavity modes that see gain as the tunable filter passband shifts. This spectral structure of the laser emission increases relative intensity noise (RIN), which degrades performance of OCT systems. Another problem is that tunable lasers using ubiquitous semiconductor gain media generally only tune well in one direction, i.e., to longer wavelengths. This is due to a nonlinear asymmetric gain effect in semiconductors that is often called the Bogatov effect. With an optical signal in a semiconductor at a given wavelength, optical waves at longer wavelengths will experience slightly higher optical gain, while optical waves at shorter wavelengths will experience slightly lower optical gain. Such asymmetric nonlinear gain distribution creates a preference for dynamic tuning in the longer wavelength direction, or up tuning, where optical gain is slightly higher, while impeding tuning in the shorter wavelength direction.

Another class of swept sources that have the potential to avoid the inherent drawbacks of tunable lasers is filtered amplified spontaneous emission (ASE) sources that combine a broadband light source, typically a source that generates light by ASE, with tunable filters and amplifiers. Some of the highest speed devices based on this configuration are described in U.S. Pat. No. 7,061,618 B2, entitled Integrated Spectroscopy System, by W. Atia, D. Flanders P. Kotidis, and M. Kuznetsov, which describes spectroscopy engines for diffuse reflectance spectroscopy and other spectroscopic applications such as OCT. A number of variants of the filtered ASE swept source are described including amplified versions and versions with tracking filters.

More recently Eigenwillig, et al. have proposed a variant configuration of the filtered ASE source in an article entitled "Wavelength swept ASE source", Conference Title: Optical Coherence Tomography and Coherence Techniques IV, Munich, Germany, Proc. SPIE 7372, 73720O (Jul. 13, 2009). The article describes an SOA functioning both as an ASE source and first amplification stage. Two Fabry-Perot tunable filters are used in a primary-tracking filter arrangement, which are followed by a second SOA amplification stage.

SUMMARY OF THE INVENTION

In general, according to one aspect, the invention features an integrated filtered ASE swept source with amplifier and tracking filter. This source comprises a micro optical bench, a source for generating broadband light, a first tunable Fabry Perot filter, installed on the bench, for spectrally filtering the broadband light from the broadband source to generate a tunable signal, an amplifier, installed on the bench, for amplifying the tunable signal, and a second tunable Fabry Perot filter, installed on the bench, for spectrally filtering the amplified tunable signal from the amplifier. The use of a single bench implementation, rather than individually packaged fiber-pigtailed optical components connected by optical fibers, yields a low cost yet higher performance system. For example, polarization control between components is generally not necessary.

In general, according to another aspect, the invention features an optical coherence tomography system. This system comprises a wavelength swept optical source, including: a micro optical bench, a source for generating broadband light, a tunable Fabry Perot filter, installed on the bench, for spectrally filtering the broadband light from the broadband source to generate a tunable signal, and an amplifier, installed on the bench, for amplifying the tunable signal. An interferometer transmits the amplified tunable signals from the wavelength swept optical source to a sample and reference arm and combines the optical signals from the sample and the reference arm to generate an interference signal. Here, the single bench implementation in an OCT system yields higher performance largely due to the improved stability of such a system.

In general, according to another aspect, the invention features an optical swept source with dual stage amplification. The source comprises a source for generating broadband light, a tunable Fabry Perot filter for spectrally filtering the broadband light from the broadband source to generate a tunable signal, a first amplifier for amplifying the tunable signal, and a second amplifier for amplifying the tunable signal from the first amplifier.

In general, according to still another aspect, the invention features an optical coherence tomography system comprising a wavelength swept optical source, including: a source for generating broadband light, a tunable Fabry Perot filter for spectrally filtering the broadband light from the broadband source to generate a tunable signal, a first amplifier for amplifying the tunable signal, and a second amplifier for amplifying the tunable signal from the first amplifier. An interferometer transmits the amplified tunable signals from the wavelength optical swept source to a sample and reference arm and combines the optical signals from the sample and the reference arm to generate an interference signal.

In general, according to still another aspect, the invention features a wavelength swept optical source comprising: a semiconductor optical amplifier for generating broadband light, a tunable Fabry Perot filter for spectrally filtering the broadband light from the broadband source to generate a tunable signal that is amplified in the second semiconductor optical amplifier, and an optical isolator for preventing back reflections into the semiconductor optical amplifier from the amplified tunable signal.

In general, according to still another aspect, the invention features a wavelength swept optical source, comprising a source for generating broadband light, a polarization beam splitter, through which the broadband light is transmitted, a tunable Fabry Perot filter for spectrally filtering the broadband light from the source to generate a tunable signal, a semiconductor optical amplifier for amplifying the tunable signal in a double pass arrangement with the amplified tunable signal being transmitted back through the tunable Fabry-Perot filter, and a polarization rotation system in between the polarization beam splitter and semiconductor amplifier.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1 is a block diagram of a swept optical source according to a first embodiment of the present invention;

FIG. 2 is a block diagram of a swept optical source according to a second embodiment of the present invention;

FIG. 3A is a block diagram of a swept optical source according to a third embodiment of the present invention;

FIG. 4A is a block diagram of a swept optical source according to a fourth embodiment of the present invention;

FIG. 4B is a block diagram of a swept optical source according to a variant of the fourth embodiment of the present invention;

FIGS. 6A-6F are plots of power (dBm) as a function of wavelength in nanometers (nm) illustrating the spectral scanning of the swept source tunable signal over the scan band and FIG. 6G is a plot of power as a function of wavelength showing the time-averaged spectrum of a filtered ASE swept source sinusoidally modulated at a 50 kHz rate with the tuning range of 100 nm;

FIGS. 7A, 7B, and 7C are top plan scale, perspective scale, and side plan schematic drawings of the first embodiment of the swept optical source.

DETAILED DESCRIPTION OF THE PREFERRED EMBODIMENTS

Figure 3B:
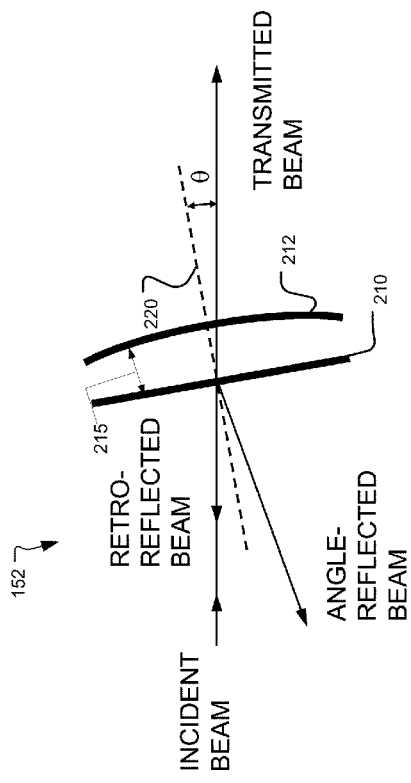
FIG. 3B is a schematic diagram of a reflective Fabry-Perot tunable filter used in the swept source.

FIG. 1 shows a first embodiment swept optical source 100 that has been constructed according to the principles of the present invention.

The swept source 100 comprises a broadband source 112 that generates a broadband optical signal. In general, the broadband signal is characterized by a continuous spectrum that extends in wavelength over at least 40 nanometers (nm) of bandwidth, full width half maximum (FWHM). Typically, the continuous spectrum extends over at least 70 nm and preferably over 100 nm or greater.

In the preferred embodiment, the broadband source 112 is an electrically pumped semiconductor chip gain medium that is bonded or attached to a bench B. Common examples of the source 110 include superluminescent light emitting diodes (SLED) and semiconductor optical amplifiers (SOA). The material system of the chip is selected based on the desired spectral operating range. Common material systems are based on III-V semiconductor materials, including binary materials, such as GaN, GaAs, InP, GaSb, InAs, as well as ternary, quaternary, and pentenary alloys, such as InGaN, InAlGaN, InGaP, AlGaAs, InGaAs, GaInNAs, GaInNAsSb, AlInGaAs, InGaAsP, AlGaAsSb, AlGaInAsSb, AlAsSb, InGaSb, InAsSb, and InGaAsSb. Collectively, these material systems support operating wavelengths from about 400 nm to 2000 nm, including longer wavelength ranges extending into multiple micrometer wavelengths. Semiconductor quantum well and quantum dot gain regions are typically used to obtain especially wide gain bandwidths. Currently, edge-emitting chips are used although vertical cavity surface emitting laser (VCSEL) chips are used in different implementations.

The use of a semiconductor chip gain medium for the source has advantages in terms of system integration since it can be bonded to a submount that in turn is directly bonded to the bench B. Other possible gain media can be used in other implementations, however. In these examples, the broadband signal is typically transmitted via optical fiber to the bench B. Such examples include solid state gain media, such as rare-earth (e.g., Yb, Er, Tm) doped bulk glass, waveguides or optical fiber.

In these examples, the output facets of the chips or gain waveguides/fibers are antireflection coated, and possibly angled, so that the gain media do not lase but instead generate broadband light via amplified spontaneous emission (ASE).

The bench B is termed a micro-optical bench and is preferably less than 10 millimeters (mm) in width and about 50 mm in length or less. This size enables the bench to be installed in a standard, or near standard-sized, butterfly or DIP (dual inline pin) hermetic package. In one implementation, the bench B is fabricated from aluminum nitride. A thermo-electric cooler is disposed between the bench B and the package (attached/solder bonded both to the backside of the bench and inner bottom panel of the package) to control the temperature of the bench B.

The broadband optical signal from the broadband source 112 is coupled to an isolator 114, which is preferably also bonded or attached to the bench B. This isolator 114 prevents feedback into the broadband source 112 that might cause it to lase or otherwise change, e.g. produce ripple in, the emission spectrum of the broadband optical signal from the broadband source.

A first tunable filter 116 functions as a tunable bandpass filter to convert the broadband signal to a narrow band tunable signal. In a current embodiment, the passband of the first tunable filter has a full width half maximum (FWHM) bandwidth of less than 20 or 10 GigaHertz (GHz), and is preferably 5 GHz or less. For spectroscopy this relatively narrow passband yields high spectral resolution. For optical coherence tomography, this high spectral resolution implies long coherence length of the source and therefore enables imaging deeper into samples, for example deeper than 5 mm. In lower performance applications, for example OCT imaging less than 1 mm deep into samples, broader FWHM passbands are sometimes appropriate, such as passbands of about 200 GHz or less.

In the current embodiment, the first tunable filter is a Fabry-Perot tunable filter that is fabricated using micro-electro-mechanical systems (MEMS) technology and is attached, such as directly solder bonded, to the bench B. Currently, the filter 116 is manufactured as described in U.S. Pat. Nos. 6,608,711 or 6,373,632, which are incorporated herein by this reference. A curved-flat resonator structure is used in which a generally flat mirror and an opposed curved mirror define a filter optical cavity, the optical length of which is modulated by electrostatic deflection of at least one of the mirrors.

The tunable optical signal that is produced by the passband of the first tunable filter 116 is amplified in a first optical amplifier 120 of a first amplification stage. Preferably the first optical amplifier is an SOA with antireflection coated and angled front and rear facets, enabling integration onto the bench B by attachment, typically via a submount.

A second isolator 118 between the first tunable filter 116 and the first amplifier 120 prevents back reflections between the front facet of the first amplifier 120 and the first tunable filter 116 from causing lasing or other spectral ripple due to parasitic reflections between these two elements. The second isolator 118 is preferably also bonded or otherwise attached to the bench B.

The amplified tunable signal from the first amplifier 120 is again passband filtered by a second tunable filter 122. This second filter 122 is preferably a tunable MEMS Fabry-Perot filter as described previously and is preferably also similarly solder-bonded or otherwise attached to the bench B via a submount. In some implementations, the only difference between the first tunable filter 116 and the second tunable filter 122 is that the second tunable filter 122 has a slightly broader passband than the first tunable filter 116, such as between 2 and 20 times broader in frequency. This second filter 122 is termed a tracking filter because it is controlled to scan synchronously with the first tunable filter 116 and thus to track tuning of the first filter. The tracking filter functions primarily to remove ASE noise introduced by the first amplifier 120 and further spectrally shape and narrow the tunable signal.

The synchronous tracking of the second tunable filter 122 with the first tunable filter 116 is controlled by a tracking controller 125 that drives both tunable filters 116, 122. Preferably, the tracking controller 125 spectrally centers the passband of the tracking tunable filter 122 on passband of the first tunable filter 116 and then tunes the two passbands together over the scanband extending over the gain bands of broadband source 112 and amplifiers 120, 126. It currently appears that tracking of filters 116, 122 is easier when they are driven sinusoidally in time at frequencies not far from their resonance by the tuning controller 125.

A third isolator 121 between the first amplifier 120 and the second tunable filter 122 prevents back reflections between the back facet of the first amplifier 120 and the second tunable filter 122 from causing lasing or other spectral ripple due to parasitic reflections between these two elements. The third isolator 121 is preferably also bonded or otherwise attached to the bench B.

The amplified tunable optical signal that is produced from the first optical amplifier 120 and filtered by the tracking filter 122 is again amplified in a second amplifier 126 of a second amplification stage. Preferably the second optical amplifier 126 is also an SOA with antireflection coated and angled front and rear facets, enabling integration onto the bench B by attachment to it. In terms of control, the second stage optical amplifier 126 is usually operated in saturation with a lower input saturation power to minimize broadband ASE contribution from this last gain stage.

A fourth isolator 124 between the front facet of the second amplifier 126 and the second tunable filter 122 prevents back reflections between the front facet of the second amplifier 126 and the second tunable filter 122 from causing lasing or other spectral ripple due to parasitic reflections between these two elements. The fourth isolator 124 is preferably also bonded or otherwise attached to the bench B.

The output tunable or swept optical signal emitted from the rear facet of the second optical amplifier 126 is transmitted to an interferometer 50 in the application where the source 100 is used as a swept source in an OCT systems. Other applications for the source include more standard spectroscopy applications such as diffuse reflectance spectroscopy and Raman spectroscopy in which the tunable signal is used to illuminate a sample 10.

If required, still further gain stages can be used. In one example a further, third SOA, third amplification stage, is added. For other applications having still higher power requirements, a rare-earth doped fiber gain stage is added after the second SOA 126.

FIG. 2 shows a second embodiment swept optical source 100 that has been constructed according to the principles of the present invention.

In this example, a first optical amplifier 140 functions in a combined role, both as a broadband ASE source and a first amplification stage. In more detail, a broadband signal is generated at a front facet of the first optical amplifier 140, preferably an SOA as described above. This broadband signal is generated by the ASE emissions of first optical amplifier 140. These emissions are coupled to a first tunable filter 116. In construction and design, the first tunable filter 116 is preferably as described in connection with the first embodiment.

The tunable signal produced by the first tunable filter is then coupled back into the front facet of the first optical amplifier 140 via an optical circulator 142. The first optical amplifier then amplifies the tunable signal, which is transmitted out of its back facet.

The amplified tunable signal is then further amplified, filtered, and otherwise conditioned by an optical train of elements isolator 121, tracking filter 122, isolator 124, and SOA 126 as described in connection with the first embodiment. Here, the tracking filter 122 tracks the first tunable filter 116 under the control of tuning controller 125.

In the preferred implementation, the elements of the second embodiment are all integrated together on a common optical bench B. The first amplifier 140 and the second amplifier 126 preferably are SOAs that are solder bonded to the bench B via submounts.

FIG. 3A shows a third embodiment swept optical source 100 that has been constructed according to the principles of the present invention.

In common with the second embodiment, a first optical amplifier 140 functions in a combined role, both as a broadband ASE source and a first amplification stage. The need for the circulator is avoided by the use of a reflective narrow-band tunable filter 152 that is preferably bonded to the bench B. This element reflects only a narrowband bandwidth tunable signal.

Otherwise, the third embodiment functions as described in connection with the second embodiment, with the narrowband signal being amplified by the first optical amplifier 140. This narrowband signal is generated by the filtered ASE emissions of first optical amplifier 140. The amplified tunable signal is then further amplified, conditioned, and filtered by an optical train of elements isolator 121, tracking filter 122, isolator 124, and SOA 126 as described in connection with the first and second embodiment. Here, the tracking filter 122 tracks the reflective narrow band filter 152 under the control of tuning controller 125

In one implementation, a tilt grating is used as the reflective narrow band filter 152. However, in the preferred embodiment, the reflective narrow band filter 152 is implemented as the tilted multi spatial mode resonator tuning element described in incorporated U.S. Pat. No. 7,415,049 B1.

In more detail, the tunable reflective optical filter 152 provides narrowband feedback into the SOA 140 in order to generate the tunable signal. Typically, the bandwidth of the feedback is less than 150 GHz wide (FWHM). More often, it is less than 15 GHz wide, FWHM.

FIG. 3B illustrates a preferred embodiment of the tunable reflective narrow band filter 152.

This tunable reflective resonant optical filter 152 would typically be referred to as a Fabry-Perot resonant filter or a Gires-Tournois interferometer (GTI). In the current embodiment, a curved-flat resonator structure is used. Thus, the resonant optical filter comprises a generally flat mirror 210 and an opposed curved mirror 212, defining a filter optical cavity 215, the optical length of which is able to be modulated. In the GTI structure, the mirror which is further away from the incident beam, which is mirror 212 in this example, typically has a much higher reflectivity than the mirror closer to the incident beam, which is mirror 210 in this example.

By angling the resonant filter 152 relative to the incident optical beam direction, and because this resonant filter 152 supports higher order spatial modes, the reflection from the tunable filter 152 into the SOA 140 can be adjusted in order to provide a narrow band spectral reflection peak, instead of the spectral reflection notch typically associated with Fabry-Perot tunable filters. Optical frequency, or wavelength, of this spectral reflection peak can be tuned by varying the mirror gap of the Fabry-Perot or GTI structure.

Figure 3C:
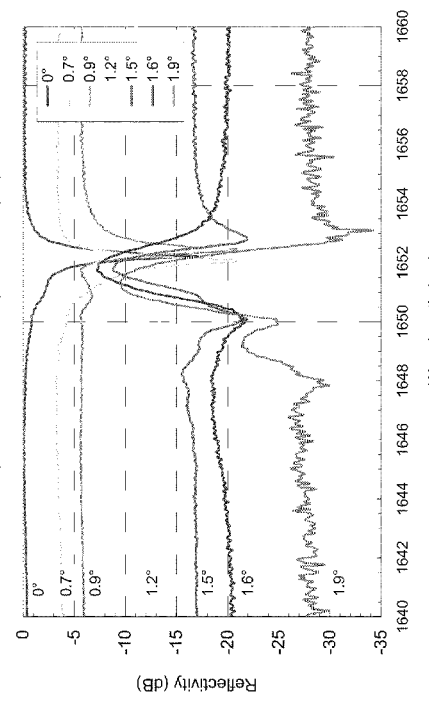
FIG. 3C is a plot of reflectivity in decibels (dB) as a function of wavelength showing the retro-reflection transfer function of the tunable filter.

FIG. 3C is a plot of measured filter retroreflection back into the incident Gaussian beam as a function of wavelength for several incident beam angles. The spectral notch observed in retro-reflection at zero degrees incident angle becomes a spectral peak when the incident angle is greater than approximately 1.5 degrees.

FIG. 4A shows a fourth embodiment swept optical source 100 that has been constructed according to the principles of the present invention.

This arrangement uses a tunable filter in a double pass arrangement to yield a self tracking design.

A broadband source 112, preferably an SOA or SLED, generates a broadband optical signal as described in connection with the first embodiment. The broadband output is transmitted through a polarization beam splitter (PBS) 161. Typically, the highly polarized output characteristic of semiconductor gain media ensures a high transmission efficiency.

A tunable bandpass filter 162 converts the broadband signal transmitted through the PBS 161 into a narrow band tunable signal. This tunable filter is preferably implemented as described in connection with the tunable filters of the first embodiment. Light that is reflected, i.e., outside the passband of the tunable filter 162, is transmitted back through the PBS 161 but stopped by isolator 160.

The polarization of the narrowband tunable signal is rotated 45 degrees by a Faraday rotator 164 and then rotated back by 45 degrees by a half-wave plate 166, such that polarization of light entering semiconductor amplifier 168 is oriented the same way as light polarization emitted by the broadband source 112. The tunable signal is then amplified in a semiconductor optical amplifier 168 in a double pass arrangement. Specifically, in a preferred embodiment, a single angled facet (SAF) SOA is used to amplify the tunable signal in a first pass through the SOA. Then reflected signal from a reflective back facet 170 is amplified in the SOA for a second time. The amplified light exiting the front facet of the SAF chip 168 passes through the half-wave plate 166 and Faraday rotator 164 again so that its polarization is orthogonal to the input broadband signal generated by the broadband source chip 112.

The exiting amplified tunable signal is then coupled out of the source 100 by the polarization beam splitter 161.

The polarization filter, or polarizer, 167 ensures that light is not fed back into the SAF chip 168 by reflections from the tunable filter 162.

As described in connection with the previous embodiments, the components of the fourth embodiment, source 112, isolator 160, PBS 161, tunable filter 162, Faraday rotator 164, HWP 166, filter 167, and SAF chip 168, are preferably attached to a common micro optical bench B, such as by solder bonding This single-filter self-tracking configuration of the filtered ASE swept source has several advantages:

1. Using a single tunable narrow filter 162, rather than two separate tunable filters for filtering and post-amplification ASE filtering, yields a simpler device with fewer components and simplified control.

2. There is no need to track closely frequency tuning of two separate narrow filters at high scan rates (50-200 kHz). At high scan rates, because of finite propagation time delays between optical components, a two-filter approach requires careful adjustment of the two filter drives' magnitudes and phase delays, such that spectrally filtered optical wave passes through the two filters at appropriately synchronized times. For a single-filter self-tracking swept source configuration, a much simplified filter tuning control is possible. Such simplified control becomes especially important when filter/swept source frequency tuning needs to be linearized in time.

3. Because of finite time delay between tunable filter 162 and the SAF chip 168, at high scan rates of greater than 10 kHz, for example, and a narrow filter of less than 10 GHz, this arrangement works best when packaged on a common optical bench B.

FIG. 4B shows a variant of the fourth embodiment swept optical source 100.

In this example, light from the broadband source 112 undergoes 45 degree rotation in a first Faraday rotator 174, which is followed by the polarization beam splitter 176 that passes this incident light. After filtering by the tunable filter 162, the polarization is rotated back by 45 degrees by a second Faraday rotator 180 to the polarization orientation of the gain SAF SOA chip 168. This polarization is the same as that of the broadband source 112. Then, the reflected double-pass amplified signal from SAF 168 is transmitted again through the second Faraday rotator 180 and bandpass filtered again by the tunable filter 162. At this point the double-filtered and double-pass amplified light that originated in source 112 is polarized such as to be coupled out of the source by the polarization beam splitter 176. Two polarization filters 172, 182 prevent back reflections into the broadband source 112 and SAF chip 168.

In other implementations, the polarization beam splitter 176 is implemented as a polarizing coating or a birefringent walk-off polarizer.

In this embodiment also, all components are preferably attached to a common optical bench B.

Figure 5:
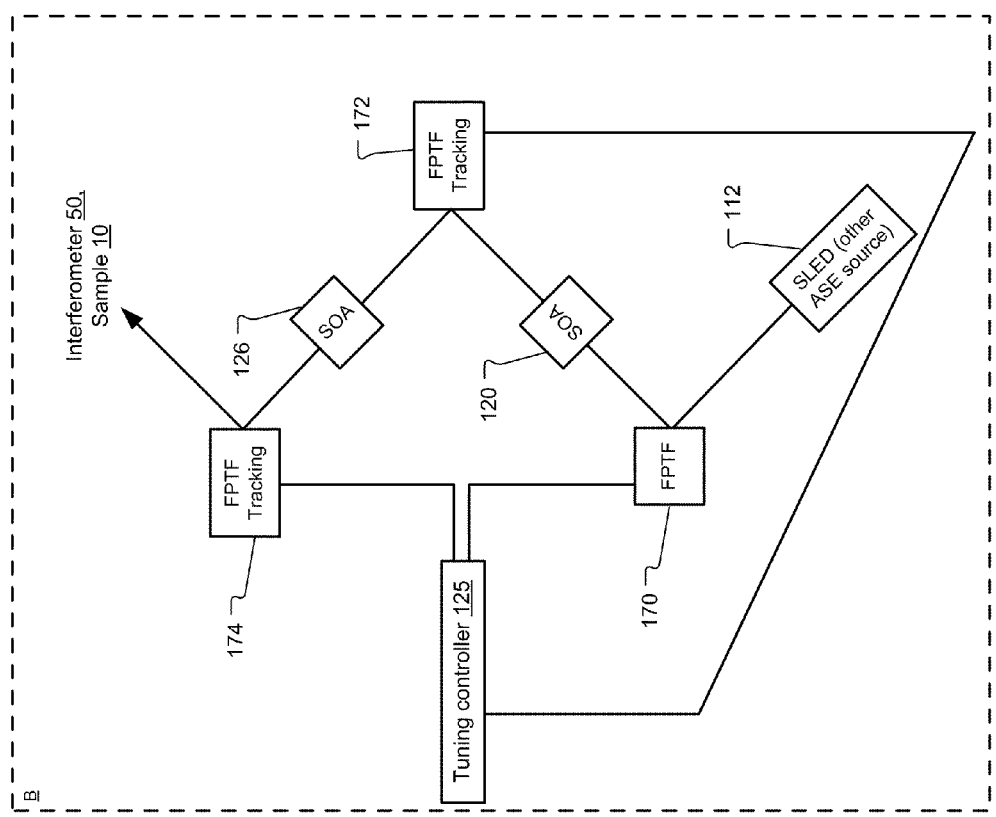
FIG. 5 is a block diagram of a swept optical source according to a fifth embodiment of the present invention.

FIG. 5 shows a fifth embodiment swept optical source 100 that has been constructed according to the principles of the present invention.

This example relies on reflective bandpass filters as described in connection with the embodiment of FIG. 3A to avoid the necessity for isolators.

In more detail, the broadband source 112, SOA or SLED chip, generates a broadband optical signal as described in connection with the first embodiment. The broadband output is transmitted to reflective bandpass filter 170. In the preferred implementation, a tunable reflective resonant optical filter is used as shown in FIG. 3B. This generates a narrowband tunable signal that is amplified by a first SOA 120.

The amplified tunable signal from the SOA 120 is filtered again by a first tracking filter 172 and then coupled into a second SOA 126 for second stage amplification. If required, a second tracking filter 174 is used to further bandpass filter the tunable signal and suppress ASE noise.

The tunable filters 170, 172, and 174 are controlled by tracking controller 125 such that the two tracking filters 172, 174 track the tuning of the first tunable filter 170.

This fifth embodiment is particularly important for operating wavelengths shorter than 1200 nm since isolators are typically physically large and expensive at and below this wavelength. Preferably, the components of the fifth embodiment are attached to a common micro optical bench B.

FIGS. 6A-6F illustrate the spectral scanning of the tunable signal 612 over the scan band defined by the gain spectrum of the gain elements. The gain spectrum of the gain elements such as the broadband source 112 and amplifiers 120, 126, 140, 168 define the useful scan band 610. Here it stretches from about 1240 to 1360 nm in wavelength.

Figure 6D:
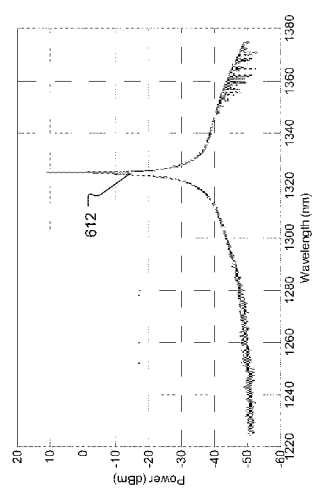
Figure 6E:
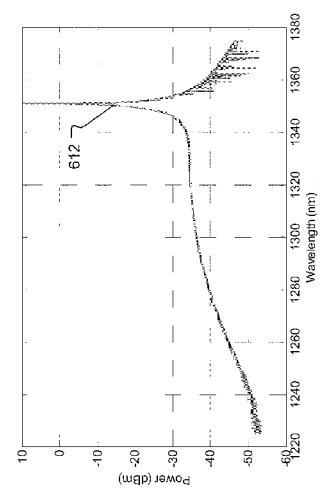
Figure 6F:
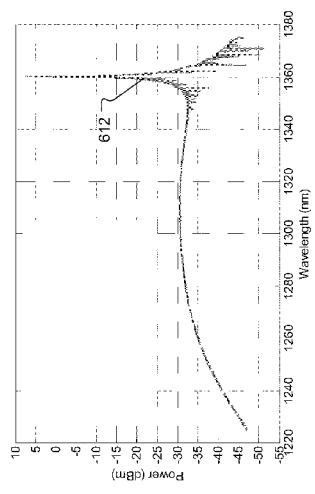
Figure 6G:
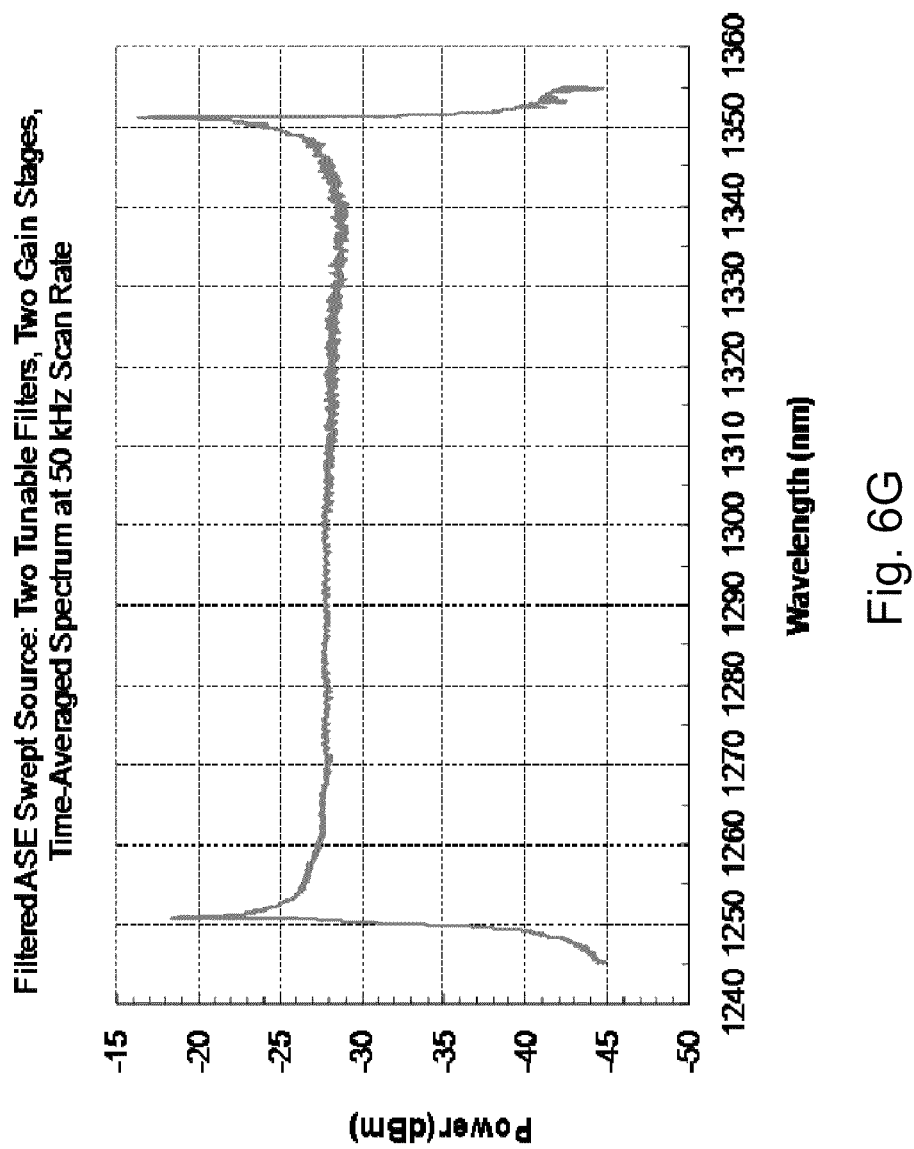

The passband of the tunable filters defines the width of the tunable signal 612. This tunable signal 612 is scanned over the scan band under control of the tuning controller 125 that orchestrates the operation of the primary tunable filter 116, 152, 162, 170 and any tracking filters 122 172, 174 of the described embodiments. Specifically, FIGS. 6A-6F illustrate the tuning of the tunable signal 612 over the scan band 610. FIG. 6G illustrates the measured time averaged spectrum of the filtered ASE swept source when the primary and tracking tunable filters are synchronously scanned at 50 kHz rate over 100 nm range from 1250 nm to 1350 nm.

Figure 7A:
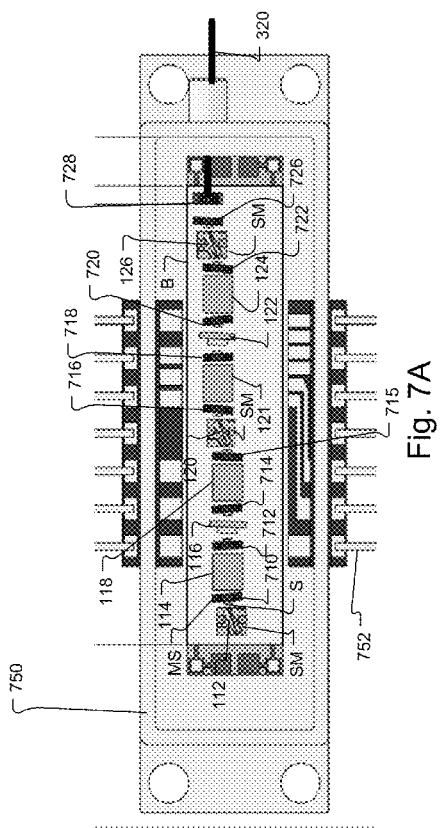
Figure 7B:
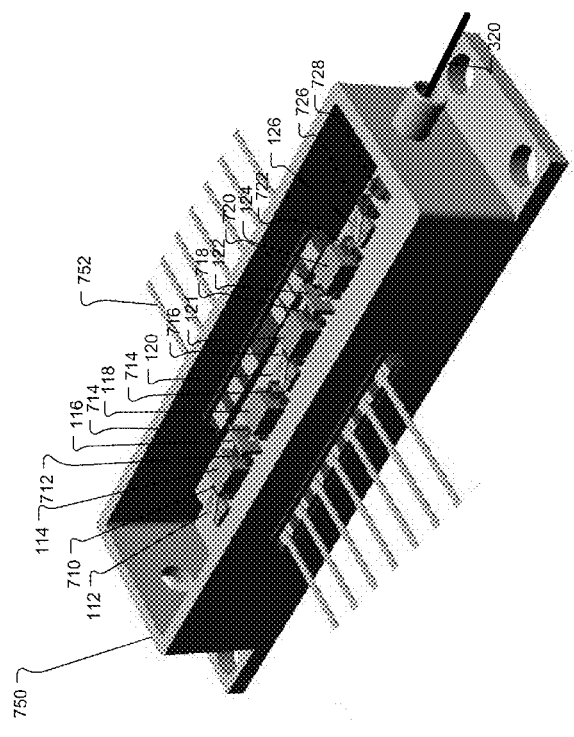

FIGS. 7A and 7B are top plan and perspective views of a swept source according to the first embodiment, showing specific implementation details and the hermetic butterfly package 750 (shown with the package's lid removed) that contains the system components.

Each of the SLED broadband source 112 and the first and second SOA amplifier chips 120, 126 are shown mounted, typically solder bonded, on respective submounts SM. These submounts are then attached, solder bonded, to the bench B.

A series of coupling lens structures are used to couple light between the components. Generally lens structures each comprise a LIGA metal mounting structure MS, which is deformable to enable post installation alignment, and an optically transmissive substrate S in which the lens is formed. The transmissive substrate S is typically solder or thermo-compression bonded to the mounting structure MS, which in turn is solder bonded to the optical bench B.

Lens structure 710 couples the broadband signal from the SLED chip 112 into the isolator 114. Lens structure 712 couples the broadband signal from the isolator 114 into the first tunable filter 116. The tunable signal from the tunable filter 116 is coupled into the second isolator 118 by lens structure 714. Lens structure 715 couples the tunable signal from the second isolator 118 into the first SOA/amplifier chip 120. Lens structure 716 couples the tunable signal from the first SOA/amplifier chip 120 into the third isolator 121. Lens structure 718 couples the tunable signal from the third isolator 121 into the tracking filter 122. Lens structure 720 couples the tunable signal from the tracking filter 122 into the fourth isolator 124. Lens structure 722 couples the tunable signal from the fourth isolator 124 into the second amplifier/SOA chip 126. Finally, lens structure 726 couples light from the second SOA 126 into an endface of optical fiber 320 that transmits the tunable signal to the interferometer and/or sample. A LIGA deformable metal fiber mounting structure 728 holds the fiber endface to the bench B. The fiber 320 extends through a sealed fiber feedthrough of the package 750

FIG. 7C shows the system in a schematic cross-section, without coupling optics for simplicity. Since the active elements typically produce heat and stable temperatures are required for long term and consistent operation, the bench B is mounted on a thermoelectric cooler 760 that connects the bench to bottom floor of the package 750. This way heat is pumped from the active elements and bench B to the hermetic package 750. The package is sealed with a lid 750L to create a hermetically sealed, controlled environment for the components on the bench B.

Figure 8:
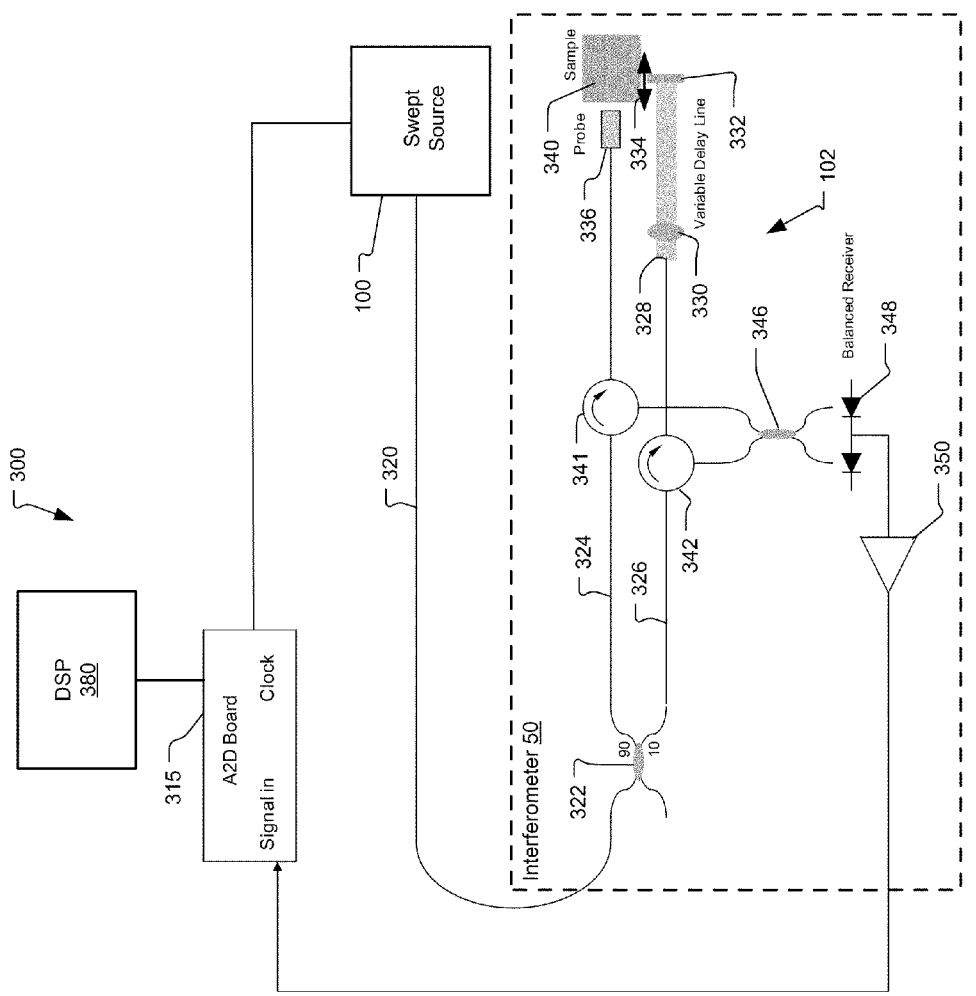
FIG. 8 is a schematic view of an OCT system in which the swept source is used in one application.

FIG. 8 shows an optical coherence analysis system 300 using the swept source 100.

In more detail, a Michelson interferometer 50 is used to analyze the optical signals from the sample 340. The tunable signal from the swept source module 100 is output on fiber 320 to a 90/10 optical coupler 322. The tunable signal is divided by the coupler 322 between a reference arm 326 and a sample arm 324 of the system.

The optical fiber of the reference arm 326 terminates at the fiber endface 328. The light exiting from the reference arm fiber endface 328 is collimated by a lens 330 and then reflected by a mirror 332 to return back.

The external mirror 332 has an adjustable fiber to mirror distance (see arrow 334). This distance determines the depth range being imaged, i.e. the position in the sample 340 of the zero path length difference between the reference arm 326 and the sample arm 324. The distance is adjusted for different sampling probes and/or imaged samples. Light returning from the reference mirror 332 is returned to a reference arm circulator 342 and directed to a 50/50 fiber coupler 346.

The fiber on the sample arm 324 terminates at the sample arm probe 336. The exiting light is focused by the probe 336 onto the sample 340. Light returning from the sample 340 is returned to a sample arm circulator 341 and directed to the 50/50 fiber coupler 346. The reference arm signal and the sample arm signal are combined in the fiber coupler 346. The combined/interference signal is detected by a balanced receiver, comprising two detectors 348, at each of the outputs of the fiber coupler 346. The electronic interference signal from the balanced receiver 348 is amplified by amplifier 350.

An analog to digital converter system 315 is used to sample the interference signal output from the amplifier 350. Frequency clock and sweep trigger signals derived from the swept source are used by the A2D board 315 to synchronize system data acquisition with the frequency tuning of the swept source.

Once a complete data set has been collected from the sample 340 by spatially raster scanning the focused probe beam point over the sample, in a Cartesian geometry x-y fashion or a cylindrical geometry theta-z fashion, and the spectral response at each one of these points is generated from the frequency tuning of the swept source 100, the digital signal processor 380 performs a Fourier transform on the data in order to reconstruct the image and perform a 2D or 3D tomographic reconstruction of the sample 340. This information generated by the digital signal processor 380 can then displayed on a video monitor.

While this invention has been particularly shown and described with references to preferred embodiments thereof, it will be understood by those skilled in the art that various changes in form and details may be made therein without departing from the scope of the invention encompassed by the appended claims.

What is claimed is:

1. A wavelength swept optical source, comprising:
    an amplified spontaneous emission source for generating broadband light;
    a tunable Fabry Perot filter for spectrally filtering the broadband light from the amplified spontaneous emission source to generate a tunable signal;
    a polarization beam splitter for transmitting the broadband light to the tunable Fabry Perot filter from the amplified spontaneous emission source;
    a polarization rotation system downstream of the polarization beam splitter for rotating the polarization;
    a semiconductor optical amplifier for amplifying the tunable signal with the amplified tunable signal being transmitted back through the tunable Fabry-Perot filter for a double pass arrangement to yield a self-tracking configuration and then through the polarization beam splitter, which provides the amplified tunable signal as an output signal and avoids coupling of the amplified tunable signal to the source or back through the semiconductor amplifier to avoid creation of a resonant cavity.

2. A wavelength swept optical source as claimed in claim 1, wherein the polarization rotation system comprises a Faraday rotator.

3. A wavelength swept optical source as claimed in claim 1, wherein semiconductor optical amplifier is a semiconductor optical amplifier with a reflective facet.

* * * * *